(12) United States Patent
Kornek et al.

(10) Patent No.: US 7,842,831 B2
(45) Date of Patent: *Nov. 30, 2010

(54) METHOD FOR THE CONTINUOUS PRODUCTION OF SILICON COMPOUNDS BEARING AMINO GROUPS

(75) Inventors: Thomas Kornek, Burghausen (DE); Jochen Rauch, Nuremberg (DE)

(73) Assignee: Wacker Chemie AG, Munich (DE)

( * ) Notice: Subject to any disclaimer, the term of this patent is extended or adjusted under 35 U.S.C. 154(b) by 575 days.

This patent is subject to a terminal disclaimer.

(21) Appl. No.: 11/721,619

(22) PCT Filed: Nov. 24, 2005

(86) PCT No.: PCT/EP2005/012586

§ 371 (c)(1), (2), (4) Date: Jun. 13, 2007

(87) PCT Pub. No.: WO2006/063667

PCT Pub. Date: Jun. 22, 2006

(65) Prior Publication Data

US 2009/0253925 A1  Oct. 8, 2009

(30) Foreign Application Priority Data

Dec. 16, 2004  (DE) ...................... 10 2004 060 627

(51) Int. Cl.
*C07C 7/10* (2006.01)

(52) U.S. Cl. ..................................... 556/424
(58) Field of Classification Search ....................... None
See application file for complete search history.

(56) References Cited

U.S. PATENT DOCUMENTS

| 3,673,233 A | 6/1972 | Golitz et al. |
| 5,210,254 A | 5/1993 | Ritscher et al. |
| 5,616,755 A | 4/1997 | Seiler et al. |
| 7,674,840 B2 | 3/2010 | Stanjek et al. |
| 2002/0065428 A1 | 5/2002 | Schwarz et al. |
| 2003/0130543 A1* | 7/2003 | Bauer et al. .................. 564/481 |
| 2004/0072921 A1 | 4/2004 | Stanjek et al. |

FOREIGN PATENT DOCUMENTS

| DE | 1 812 564 | 6/1970 |
| DE | 195 13 976 A1 | 3/1996 |
| DE | 693 06 288 T2 | 4/1997 |
| DE | 199 41 283 A1 | 5/2000 |
| DE | 103 53 063 A1 | 6/2005 |
| EP | 0 527 007 A1 | 2/1993 |
| EP | 0 702 017 A1 | 3/1996 |
| EP | 1 209 162 A2 | 5/2002 |
| GB | 686068 | 1/1953 |
| JP | 4149183 A | 5/1992 |
| JP | 6211878 A | 8/1994 |
| JP | 2001340753 A | 12/2001 |
| JP | 2004518801 | 6/2004 |
| JP | 2004337649 A | 12/2004 |
| WO | 01/85737 A1 | 11/2001 |
| WO | 02/066532 A1 | 8/2002 |
| WO | 2005/047298 A1 | 5/2005 |

OTHER PUBLICATIONS

Chan et al., J. Chem. Soc. Chem. Comm., 1280-81 (1988).*
English Abstract Corresponding to DE 195 13 976 A1.
English Abstract Corresponding to DE 103 53 063 A1.
English Abstract Corresponding to DE 199 41 283 A1.
English Abstract Corresponding to WO 2005/047298 A1.
English Abstract Corresponding to WO 01/85737 A1.

* cited by examiner

*Primary Examiner*—Daniel M Sullivan
*Assistant Examiner*—Yevegeny Valenrod
(74) *Attorney, Agent, or Firm*—Brooks Kushman P.C.

(57) ABSTRACT

N-organylaminoorganyl- and N,N-diorganylaminoorganyltriorganylsilanes are prepared continuously with high space/time yield, high product purity, and low halide content, while simultaneously increasing process safety, by introducing haloalkyltriorganylsilane and a 1 to 100 fold motor excess of organylamine into a continuous reactor with a residence time which may be less than 10 minutes, thus minimizing competing side reactions.

14 Claims, No Drawings

METHOD FOR THE CONTINUOUS PRODUCTION OF SILICON COMPOUNDS BEARING AMINO GROUPS

CROSS-REFERENCE TO RELATED APPLICATION

This application is the U.S. national phase of PCT Appln. No. PCT/EP2005/012586 filed Nov. 24, 2005, which claims priority to German application de 10 2004 060 627.7 filed Dec. 16, 2004.

BACKGROUND OF THE INVENTION

1. Field of the Invention

The invention relates to a process for continuously preparing (N-organylaminoorganyl)- and (N,N-diorganylaminoorganyl)triorganylsilanes from corresponding triorganylsilylorganyl halides and N-organyl- or N,N-diorganylamines.

2. Description of the Related Art

The prior art discloses various processes for preparing (N-organylaminoorganyl)- and (N,N-diorganylaminoorganyl)triorganylsilanes. Among the processes described to date, the reaction of (haloorganyl)silanes with corresponding amines has been found to be by far the most favorable with regard to process technology and economic aspects.

What is advantageous in this case is in particular the high availability of (chloroalkyl)silanes, which are obtainable by means of photochlorination of alkyl-silanes or hydrosilylation of corresponding halogen-substituted olefins onto Si—H-containing compounds, and find use, for example, as intermediates for the synthesis of a multitude of organofunctional silanes. Moreover, it is possible in this process to employ a large number of readily available primary and secondary amines to form the (N-organylaminoorganyl)- and (N,N-diorganylaminoorganyl) triorganylsilanes, which enables a very wide field of use of the process and, as a result, inexpensive product change on existing industrial manufacturing plants.

GB 686,068 A discloses (amino)-, (N-organylamino)- and (N,N-diorganylaminomethyl)- or (N,N-diorganylaminoethyl)triorganylsilanes. Moreover, GB 686,068 A describes a process for reacting corresponding (chloromethyl)- or (bromomethyl)triorganosilanes with ammonia, a primary or secondary amine at temperatures of at least 50° C. to prepare the (aminoorganyl)-, (N-organylaminoorganyl)- and (N,N-diorganylaminoorganyl)triorganylsilanes. In general, the (chloromethyl)- or (bromomethyl)triorganosilanes were initially charged in a flask or autoclave depending on the boiling point of the amine compounds used, and heated to temperatures above 100° C., preferably 110-130° C. In the case of relatively high-boiling amines (e.g. cyclohexylamine), the mixing sequence was reversed and the (chloromethyl)- or (bromomethyl)-triorganosilanes were added to the heated amine. The reaction time, depending on the amine compound to be converted, was from 2 to 8 hours.

The (aminomethyl)silane derivatives are prepared by the process described in DE 1812564 A1, by reacting a (chloromethyl)- or (bromomethyl)silane derivative with ammonia or a primary amine. The reaction is effected at temperatures of 80 or 100° C. within a period of 3 or 2 hours, the amine already having been initially charged completely at the start of the reaction in a molar excess of 1:3.2-6.

The processes described in GB 686068 A and DE 1812564 A1 have comparatively long reaction times of several hours. The achievable yields are nevertheless low, which is a consequence of the long reaction times and the associated increased formation of by-products, among other factors (on this subject, see below). Moreover, the products are not obtained in the required purity and have to be purified in a complicated manner before their further use. For example, the products obtained by the process described contain large amounts of ionic chloride or bromide. This limits their industrial use without purification, for example for use in sealants to be applied to metallic surfaces, the ionic content results in promotion of corrosion, among other reasons.

The chloride- or bromide-containing impurities which occur here are in particular the hydrochlorides or hydrobromides of the amines used in the synthesis or the hydrochlorides or hydrobromides of the target compounds.

In this context, it has been observed that mixtures of (aminomethyl)silanes and such hydrochlorides or -bromides can lead, at the relatively high temperatures necessary during preparation and distillative purification of the target compounds, to an undesired and exothermic decomposition of the target compounds with cleavage of the Si—C bond and simultaneous formation of corresponding N-methylated amines. The N-methylamines thus formed influence the course of the process in a very undesired manner. This effect appears to correlate with the basicity of the amine compound to the extent that such decomposition reactions are favored with decreasing basicity of the corresponding (aminomethyl) silane. For this reason, a low halide content of the (aminomethyl)silanes is also necessary from a safety point of view.

The prior art discloses processes for reducing halide contents in alkoxysilanes, for example those which are based on the precipitation of the dissolved halide by adding alkalimetal alkoxide or alkaline earth metal alkoxide salts (for example EP 0702017 A1, DE 69306288 T2, DE 19513976 A1), but superstoichiometric amounts of the salts are needed in this case for the simple and efficient reduction of the halide content, since merely stoichiometric amounts cannot achieve the desired complete halide removal. All (aminomethyl)silanes investigated to date have an unfavorable tendency under these conditions, e.g. the simultaneous presence of free alcohols and strong bases, to participate in decomposition reactions. An alternative process which should enable reductions of chloride contents in alkoxysilanes by introduction of ammonia is described in DE 19941283 A1, but the possibility of using (aminoalkyl)alkoxysilanes is explicitly ruled out in this process.

Moreover, it was observed that the decomposition of (aminomethyl)silanes previously mentioned takes place not only in the presence of hydrochlorides or alcohols and bases, but rather, in particular, even the sole presence of alcohols may be sufficient to bring about the undesired formation of corresponding N-methylamines. The N-methylated amine derivatives thus formed compete during the reaction with unmethylated amine still present for reaction with the (halomethyl) silane, and lead finally lead to the formation of (N-methylaminomethyl)silanes which cannot be removed again by distillation from the target compounds. To avoid this undesired side reaction, it is therefore necessary to ensure the absence of alcohols in the reaction mixture. When at least one of the organyl radicals on the silicon atom is an alkoxy group, it is possible to use only amines with low water content in the process, since alcohols can otherwise be released by preceding reaction of the silane with water present in the amine.

Moreover, the heating of the completely premixed solution of silane and amine described in DE 1812564 A1 is of concern for an industrial scale reaction for safety reasons owing to the exothermic reaction of the two components.

DE 10353063 discloses an improved process for preparing (N-organylaminoorganyl)- and (N,N-diorganylaminoorganyl)triorganylsilanes, in which the starting silane is initially charged and heated and then the corresponding amine is added continuously.

Moreover, the halide contents in the target compounds can be reduced by adding nonpolar solvents to the crude mixtures and then removing the precipitated salts. The use of low-water content amines prevents the release of alcohols during the synthesis, and hence also the formation of by-products. Surprisingly, it was also possible to remove the amine hydrohalide or (aminomethyl)silane hydrohalide from the mixture during the process by salt exchange with ammonia, which also prevents the formation of the N-methylated by-products. It was surprisingly possible to obtain chloride-free (aminomethyl)silanes preferentially by introducing ammonia into the crude product or isolated end product, even one though skilled in the art would expect the opposite from the teaching of DE 19941283 A1. The improved process described in DE 10353063 was, however, performed in batch operation and thus did not offer the desired increase in space-time yield and product quality.

SUMMARY OF THE INVENTION

It was thus an object of the invention to provide a process for preparing (N-organylaminoorganyl)- and (N,N-diorganylaminoorganyl)triorganylsilanes which solves the problems of the prior art, and especially makes the products available with short reaction times in high yields and simultaneously high purities. These and other objects are surprisingly achieved by virtue of a process in which the starting silane and the corresponding low-water content amine are reacted in a continuously operated reactor with low residence times.

DETAILED DESCRIPTION OF THE PREFERRED EMBODIMENT(S)

The invention thus provides a process for preparing N-(organylaminoorganyl)- and (N,N-diorganylaminoorganyl)triorganylsilanes of the general formula (1)

$$R_{3-n}R^1{}_nSi-R^2-NR^3R^4 \quad (1)$$

where
R is a hydrocarbon radical or an alkoxy radical which has 1-10 carbon atoms and is saturated or unsaturated, branched or unbranched, substituted or unsubstituted,
$R^1$ is a hydrocarbon radical which has 1-10 carbon atoms and is saturated or unsaturated, branched or unbranched, substituted or unsubstituted,
$R^2$ is a hydrocarbon radical which has 1-10 carbon atoms and is saturated or unsaturated, branched or unbranched, substituted or unsubstituted,
$R^3$, $R^4$ are each hydrogen or a hydrocarbon radical which has 1-10 carbon atoms and is saturated or unsaturated, branched or unbranched, substituted or unsubstituted, with the proviso that $R^3$, $R^4$ are each the same or different and are optionally bonded to one another, in which case the resulting ring may also contain heteroatoms,
X is chlorine, bromine or iodine, and
n is equal to 1, 2 or 3
by reacting cyclic or acyclic amines of the general formula (2)

$$H-NR^3R^4 \quad (2)$$

which have a water content of from 0 to 20,000 ppm
with (haloorganyl)silanes of the general formula (3)

$$R_{3-n}R^1{}_nSi-R^2-X \quad (3)$$

characterized in that the reaction comprises the following steps a) uniformly adding the (haloorganyl)silane of the general formula (3) and the amine of the general formula (2) to a continuously operated reactor at a temperature of from 50 to 250° C., the residence time of the reactants used in the reactor being between 1 min and 120 min and the amine of the general formula (2) being used with a 1- to 100-fold excess, b) and optionally additionally adding nitrogen compounds simultaneously with or offset in time from the addition of the (haloorganyl)silane and of the amine and removing the adducts formed.

The principle feature of the invention is that the reaction is effected continuously and, in the process, the (haloorganyl)silane of the general formula (3) is added uniformly to a from 1- to 100-fold excess of the amine of the general formula (2) at a temperature of from 50 to 250° C. in a continuously operated reactor, the residence time of the silane in the reactor being between 1 min and 120 min. If appropriate, nitrogen compounds which form readily removable liquid or solid adducts with the hydrohalides formed as a primary product with salt exchange and simultaneously obtaining the parent amines may optionally be added. The optional addition of the nitrogen compounds can be effected simultaneously with or offset in time from the addition of the (haloorganyl)silane.

The optional step b) thus comprises the salt exchange of the hydrohalides formed by adding nitrogen compounds during or after the addition of the (haloorganyl)silane and of the amine and the removal of the ammonium salts formed after the addition has ended.

Suitable nitrogen compounds in the optional process step b) are in principle those compounds which form readily removable solid or liquid adducts on contact with hydrogen halides. Particular preference is given to adding ammonia as the nitrogen compound.

The addition of the nitrogen compound, especially of ammonia, achieves a salt exchange of the hydrohalides formed, and the adducts formed, especially ammonium salts, can be removed easily.

Compared to batchwise operation, the continuous reaction has the advantage that varying product compositions, as are typical for batch processes, can be avoided. The reaction times can be reduced significantly by the continuous reaction, which increases the economic viability of the process. Equally, the shortening of the reaction time allows the formation of undesired by-products to be further reduced significantly.

The process is generally performed at temperatures between 50 and 250° C. In order to achieve a compromise between economically viable reaction times (residence times) and a reaction which leads to a minimum level of by-products, temperatures of from 100 to 220° C., especially of from 150° C. to 200° C., have been found to be particularly advantageous. At significantly lower temperatures, the reaction times (residence times) lengthen; in the case of higher temperatures, significantly more by-product formation occurs.

Based on the silane component, the amine is generally used in molar ratios of from 1 to 100, preferably from 2 to 50, more preferably from 4 to 20, especially from 4 to 10.

The process allows, depending on the selected temperature, conversion times (in continuous operation, better described by the term "residence times") in the region of a few minutes to be achieved. The residence time may generally be from 1 to 120 min, preferably from 1 to 60 min. Particularly advantageous residence times have been found to be less than or equal to 10 min.

In a particularly preferred embodiment of the process according to the invention, the reaction parameters are selected as follows: molar silane component/amine ratio of from 4 to 20, especially from 4 to 10; temperature 150-200° C.; residence time of less than or equal to 10 min.

Since some mixtures of the resulting target products with particular amine hydrochlorides exhibit very exothermic reactions, especially at relatively high temperatures, the process is optionally performed in the presence of a hydrogen halide scavenger which converts the amine hydrochlorides mentioned to their corresponding amines. This embodiment is preferred. Preferred hydrogen halide scavengers in this context are ammonia and those nitrogen compounds which form easily removable solid or liquid adducts on contact with hydrogen halides.

For the performance of the process, suitable reactors are all continuously operable reactors which correspond to the state of the art, for example tubular reactors, loop reactors, stirred tanks or battery reactors.

When, depending on the requirements on the product, only small amounts of unconverted starting silane are tolerable, preference is given to using a tubular reactor, since this allows the problem of backmixing of the reaction medium in the reactor, which leads to the enrichment of starting silane in the target product, to be avoided. In this context, all types of statically or dynamically mixed tubular reactors corresponding to the prior art are usable, especially those which are equipped in the interior with stirrer blades which can be driven by a stirrer shaft. In this context, preference is given to those tubular reactors which are divided over the length by internals into individual chambers which are each mixed by at least one stirrer unit driven by a central shaft. The number of chambers is between 2 and 200, preferably between 10 and 100 and more preferably between 20 and 80.

Possible embodiments for hydrocarbon radicals of $R^1$, $R^3$ and $R^4$ are each independently alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as the o-, m-, and p-tolyl radicals xylyl radicals and ethylphenyl radicals; and aralkyl radicals such as the benzyl radical, the α- and the β-phenylethyl radicals; and combinations thereof linked by heteroatoms such as N, O, S, P.

Preferably not more than one of the $R^3$ and $R^4$ radicals is hydrogen.

Moreover, the $R^3$ and $R^4$ radicals may be connected directly or by heteroatoms, so as to give rise to cyclic —$NR^3R^4$ structures with structural inclusion of the nitrogen atom. Examples thereof are the morpholino, piperidino or pyrrolidino radicals, which are also preferred. In addition, the $NR^3R^4$ radical is preferably the N,N-bis(N',N'-dimethylaminopropyl) radical. $R^1$ is preferably a methyl, ethyl, iso- and n-propyl, iso- and n-butyl, pentyl, hexyl, heptyl, octyl, nonyl, decyl, phenyl, benzyl or allyl radical.

The $R^3$ and $R^4$ radicals are preferably selected from the preferred $R^1$ radicals and also from hydrogen, cyclohexyl or phenyl radicals. In a particularly preferred embodiment, the $R^3$ radical is the phenyl or cyclohexyl radical and the $R^4$ radical is hydrogen.

The R radical is defined as $R^1$ or $OR^1$. R is preferably the methoxy, ethoxy, iso- and n-propoxy, butoxy, phenoxy, benzyloxy or allyloxy radical.

The $R^2$ radical is preferably a methylene, ethylene and propylene group, more preferably the methylene group.

The X radical is defined as chlorine, bromine or iodine, preferably chlorine or bromine, more preferably chlorine.

n has the value of 0, 1, 2 or 3, preferably 1, 2 or 3.

The water content of the amines of the general formula (2) is preferably from 0 to 20,000 ppm, more preferably from 0 to 5000 ppm, and most preferably from 0 to 1000 ppm.

It was possible with the process of the invention to obtain (N-organylaminoorganyl)- and (N,N-diorganylaminoorganyl) triorganylsilanes in quantitative yield from corresponding triorganylsilylorganyl halides and N-organyl- or N,N-diorganylamines. The process can in particular be implemented in a simple manner without risk on an industrial scale.

The immediate process product of the process according to the invention can be worked up even further in optional additional process steps.

Preference is given to first removing the adducts formed after the introduction of the nitrogen compounds, especially ammonia, optionally as solids.

The invention further provides a process which comprises one or more of the following further steps:

c) removing the excess amine in the direct process product d) adding a nonpolar solvent to precipitate ammonium compounds still dissolved with subsequent removal of the ammonium salts formed e) distilling the product.

The purity of the (N-organylaminoorganyl)- and (N,N-diorganylaminoorganyl)triorganylsilanes is at least 85%. This purity can be increased to above 95% by means of an optional downstream distillation step e) of the product. Excess amine in the product can be removed in an optional additional step c), especially employing reduced pressure.

The resulting crude product can also, in an optional step d), be admixed by adding a nonpolar solvent for the precipitation of ammonium compounds which are still dissolved. The ammonium salts thus precipitated can subsequently be removed easily. In this way, the content of ionic halides, especially chloride or bromide, can be reduced to a particularly great extent, and no ammonium compounds are entrained into the distillation unit in an optionally performed distillation step of the crude product.

The particular advantages the process offers over the prior art are that it is possible to shorten the reaction, times through the selection of suitable reaction process temperature, to significantly and surprisingly reduce reaction times to the minute range with complete reaction conversion. At the same time, the use of optimized excesses of amine of the general formula (2) allows the formation of by-products to be reduced significantly. In addition, the continuously operated process has the advantage that products are obtained with constant composition and quality. Moreover, the process is also found to be significantly more favorable from the point of view of operational safety with respect to the exothermic reactions previously mentioned, since the reactor volume in continuous operation can be considerably smaller compared to processes performed batchwise with a uniform amount of target product.

In the examples which follow, unless stated otherwise in each case, all amount and percentage data are based on the weight and all pressures on 0.10 MPa (abs.).

EXAMPLES

Comparative Example 1

Not Inventive

In a 500 ml four-neck flask with reflux condenser, precision glass stirrer, thermometer and gas inlet tube, 298 g of dry aniline were heated to 130° C. and admixed with 124 g of (chloromethyl)methyl-dimethoxysilane with stirring within 60 min. When the addition had ended, ammonia was passed through the mixture with uniform temperature with stirring until no further reaction was observed (approx. 60 min). Thereafter, excess aniline was removed under reduced pressure, and the suspension was cooled to 30° C. and then admixed with 150 ml of isohexane. Subsequently, the white precipitate formed was filtered through a suction filter and washed with 2×80 ml of isohexane. Filtrate and wash solutions were combined and freed from the solvent under reduced pressure. The subsequent fractional distillation gave 160 g (95% yield) of (N-phenylaminomethyl)dimethoxy(methyl)silane with a chloride content of <20 ppm.

Example 2

Four parts of dry aniline, one part of (chloromethyl)-dimethoxy(methyl)silane and one part of ammonia were metered uniformly into a tubular reactor (length 3.60 m, internal diameter 0.05 m) with a rotating stirrer shaft (approx. 800-1200 revolutions per minute), onto which a total of 60 stirrer blades of height 0.01 m are mounted at a distance of 0.06 m, at a temperature of 170° C. so as to give rise to a mean residence time of the mixture in the reactor of 10 minutes. The crude mixture thus obtained was worked up analogously to example 1, which resulted in identical yields and product purities.

Example 3

Example 2 was repeated with the modification that aniline, (chloromethyl)dimethoxy(methyl)silane and ammonia were metered in at a temperature of 185° C. so as to give rise to a mean residence time of the mixture in the reactor of 5 minutes. The crude mixture thus obtained was worked up analogously to example 1, which resulted in identical yields and product purities.

The invention claimed is:

1. A process for preparing N-(organylaminoorganyl)- and (N,N-diorganylaminoorganyl)triorganylsilanes of the formula (1)

$$R_{3-n}R^1{}_nSi-R^2-NR^3R^4 \qquad (1)$$

where
R is a hydrocarbon radical or an alkoxy radical which has 1-10 carbon atoms and is saturated or unsaturated, branched or unbranched, substituted or unsubstituted,
$R^1$ is a hydrocarbon radical which has 1-10 carbon atoms and is saturated or unsaturated, branched or unbranched, substituted or unsubstituted,
$R^2$ is a hydrocarbon radical which has 1-10 carbon atoms and is saturated or unsaturated, branched or unbranched, substituted or unsubstituted, $R^3$, $R^4$ are each hydrogen, or a hydrocarbon radical which has 1-10 carbon atoms and is saturated or unsaturated, branched or unbranched, substituted or unsubstituted, with the proviso that $R^3$, $R^4$ may each be the same or different and are optionally bonded to one another, in which case the resulting ring may also contain heteroatoms, with the proviso that not more than one of $R^3$ and $R^4$ is hydrogen,
X is chlorine, bromine or iodine,
n is equal to 1, 2 or 3 and
the process comprising continuously reacting cyclic or acyclic amines of the formula (2)

$$H-NR^3R^4 \qquad (2)$$

which have a water content of from 0 to 20,000 ppm with (haloorganyl)silanes of the formula (3)

$$R_{3-n}R^1{}_nSi-R^2-X \qquad (3)$$

in the steps of:
a) uniformly adding the (haloorganyl)silane of the formula (3) and the amine of the formula (2) to a continuous reactor at a temperature of from 50 to 250° C., the residence time of the reactants in the reactor being between 1 min and 120 min and the amine of the general formula (2) being used in a 1- to 100-fold molar excess, and
b) adding at least one nitrogen compound which forms a removable liquid or solid adduct with hydrogen halides and removing adducts formed therewith.

2. The process of claim 1, wherein the process is performed in a statically or dynamically mixed tubular reactor.

3. The process of claim 1, wherein the water content of the amine of the formula (2) is from 0 to 1000 ppm.

4. The process of claim 1, wherein the $R^3$ and $R^4$ radicals are each independently selected from the group consisting of cyclohexyl, phenyl and hydrogen, or are bonded directly or by heteroatoms, so as to give rise to cyclic —$NR^3R^4$ structures with structural inclusion of the nitrogen atom.

5. The process of claim 4, wherein the cyclic —$NR^3R^4$ structure is a morpholino, piperidino or pyrrolidino radical.

6. The process of claim 1, wherein the nitrogen compound in the optional process step b) is ammonia.

7. The process of claim 1, wherein the process further comprises one or more of the following additional steps:
c) removing the excess amine from a direct process product,
d) adding a nonpolar solvent to precipitate ammonium compounds still dissolved, and subsequently removing the ammonium salts formed, and
e) distilling the product.

8. The process of claim 1, wherein the molar excess of the amine of the formula (2) is from 4 to 20.

9. The process of claim 1, wherein the molar excess of the amine of the formula (2) is from 4 to 10.

10. The process of claim 1, which is carried out at a pressure of about 0.10 MPa.

11. The process of claim 1, where ammonia is introduced into the continuous reactor along with the amine of formula (2).

12. The process of claim 7, wherein the molar excess of the amine of the formula (2) is from 4 to 20.

13. The process of claim 7, wherein the molar excess of the amine of the formula (2) is from 4 to 10.

14. The process of claim 7, where ammonia is introduced into the continuous reactor along with the amine of formula (2).

* * * * *